(12) United States Patent
Patterson et al.

(10) Patent No.: US 7,896,899 B2
(45) Date of Patent: Mar. 1, 2011

(54) METALLIC COILS ENLACED WITH BIOLOGICAL OR BIODEGRADABLE OR SYNTHETIC POLYMERS OR FIBERS FOR EMBOLIZATION OF A BODY CAVITY (75) Inventors: William R. Patterson, Irvin, CA (US); Earl Slee, Laguna Niguel, CA (US); Tom Wilder, Newport Beach, CA (US); Thomas McCarthy, San Clemente, CA (US); Brian Strauss, Trabuco Canyon, CA (US); Herman Monstadt, Bochum (DE); Hans Henkes, Bochum (DE)

(73) Assignee: Micro Therapeutics, Inc., Irvine, CA (US)

( * ) Notice: Subject to any disclaimer, the term of this patent is extended or adjusted under 35 U.S.C. 154(b) by 1306 days.

(21) Appl. No.: 11/134,998

(22) Filed: May 23, 2005

(65) Prior Publication Data
US 2006/0036281 A1 Feb. 16, 2006

Related U.S. Application Data (60) Provisional application No. 60/573,710, filed on May 21, 2004.

(51) Int. Cl.
*A61M 29/00* (2006.01)
(52) U.S. Cl. .................. 606/200; 606/191; 623/23.72
(58) Field of Classification Search .................. 606/191, 606/200
See application file for complete search history.

(56) References Cited

U.S. PATENT DOCUMENTS

| 3,174,851 A | 3/1965 | Buehler et al. |
| 3,753,700 A | 8/1973 | Harrison et al. |
| 3,834,394 A | 9/1974 | Hunter et al. |
| 4,402,319 A | 9/1983 | Handa et al. |
| 4,545,367 A | 10/1985 | Tucci |
| 4,677,191 A | 6/1987 | Tanaka et al. |
| 4,994,069 A | 2/1991 | Ritchart et al. |
| 5,122,136 A | 6/1992 | Guglielmi et al. |
| 5,226,911 A | 7/1993 | Chee et al. |
| 5,256,146 A | 10/1993 | Ensminger et al. |
| 5,304,194 A | 4/1994 | Chee et al. |
| 5,354,295 A | 10/1994 | Guglielmi et al. |
| 5,382,259 A | 1/1995 | Phelps et al. |
| 5,382,260 A | 1/1995 | Dormandy et al. |
| 5,423,829 A | 6/1995 | Pham et al. |
| 5,423,849 A | 6/1995 | Engelson et al. |
| 5,443,478 A | 8/1995 | Purdy |
| 5,476,472 A | 12/1995 | Dormandy et al. |

(Continued)

FOREIGN PATENT DOCUMENTS
EP 0368571 5/1990

OTHER PUBLICATIONS

Annex to Form PCT/ISA/206, Communication Relating to the Results of the Partial International Search, mailed Oct. 10, 2005 in corresponding Application No. PCT/US/2005/018087, Henkes et al., Neurosurgery 54, No. 2, 268 (2004).

(Continued)

*Primary Examiner* — (Jackie) Tan-Uyen T. Ho
*Assistant Examiner* — Melissa Ryckman
(74) *Attorney, Agent, or Firm* — Knobbe Martens Olson & Bear LLP (57) ABSTRACT

The invention provides for vaso-occlusive coils comprising fibers.

48 Claims, 4 Drawing Sheets

U.S. PATENT DOCUMENTS

| | | |
|---|---|---|
| 5,485,496 A | 1/1996 | Lee et al. |
| 5,522,822 A | 6/1996 | Phelps et al. |
| 5,540,680 A | 7/1996 | Guglielmi et al. |
| 5,549,624 A | 8/1996 | Mirigian et al. |
| 5,582,619 A | 12/1996 | Ken |
| 5,624,449 A | 4/1997 | Pham et al. |
| 5,658,308 A | 8/1997 | Snyder |
| 5,700,258 A | 12/1997 | Mirigian et al. |
| 5,746,734 A | 5/1998 | Dormandy, Jr. et al. |
| 5,766,219 A | 6/1998 | Horton |
| 5,833,705 A | 11/1998 | Ken et al. |
| 5,843,118 A | 12/1998 | Sepetka et al. |
| 5,853,418 A | 12/1998 | Ken et al. |
| 5,855,578 A | 1/1999 | Guglielmi et al. |
| 5,891,192 A | 4/1999 | Murayama et al. |
| 5,895,385 A | 4/1999 | Guglielmi et al. |
| 5,911,731 A | 6/1999 | Pham et al. |
| 5,925,037 A | 7/1999 | Guglielmi et al. |
| 5,935,145 A * | 8/1999 | Villar et al. ............ 606/191 |
| 5,941,888 A | 8/1999 | Wallace et al. |
| 5,947,962 A | 9/1999 | Guglielmi et al. |
| 5,947,963 A | 9/1999 | Guglielmi |
| 5,976,126 A | 11/1999 | Guglielmi et al. |
| 5,976,162 A | 11/1999 | Doan et al. |
| 5,980,550 A | 11/1999 | Eder et al. |
| 5,984,929 A | 11/1999 | Bashiri et al. |
| 6,001,092 A | 12/1999 | Mirigian et al. |
| 6,004,338 A | 12/1999 | Ken et al. |
| 6,010,498 A | 1/2000 | Guglielmi |
| 6,013,084 A * | 1/2000 | Ken et al. ............ 606/108 |
| 6,066,133 A | 5/2000 | Guglielmi et al. |
| 6,083,220 A | 7/2000 | Guglielmi |
| 6,123,714 A | 9/2000 | Gia et al. |
| 6,143,007 A | 11/2000 | Mariant et al. |
| 6,146,373 A | 11/2000 | Cragg et al. |
| 6,187,027 B1 | 2/2001 | Mariant et al. |
| 6,193,728 B1 | 2/2001 | Ken et al. |
| 6,221,066 B1 | 4/2001 | Ferrera et al. |
| 6,231,586 B1 | 5/2001 | Mariant |
| 6,280,457 B1 | 8/2001 | Wallace et al. |
| 6,287,318 B1 | 9/2001 | Villar et al. |
| 6,299,627 B1 | 10/2001 | Eder et al. |
| 6,423,085 B1 | 7/2002 | Murayama et al. |
| 6,468,266 B1 | 10/2002 | Bashiri et al. |
| 6,485,524 B2 | 11/2002 | Strecker |
| 6,511,468 B1 | 1/2003 | Cragg et al. |
| 6,558,367 B1 | 5/2003 | Cragg et al. |
| 6,964,657 B2 | 11/2005 | Cragg et al. |
| 7,070,607 B2 | 7/2006 | Murayama et al. |
| 7,238,194 B2 | 7/2007 | Monstadt et al. |
| 7,300,458 B2 | 11/2007 | Henkes et al. |
| 7,323,000 B2 | 1/2008 | Monstdt et al. |
| 7,485,317 B1 | 2/2009 | Murayama et al. |
| 7,524,322 B2 | 4/2009 | Monstdt et al. |
| RE41,029 E | 12/2009 | Guglielmi et al. |
| 2002/0087184 A1 | 7/2002 | Eder et al. |
| 2003/0014073 A1 | 1/2003 | Bashiri et al. |
| 2003/0040733 A1 | 2/2003 | Cragg et al. |
| 2003/0225365 A1 | 12/2003 | Greff et al. |
| 2004/0098029 A1 | 5/2004 | Teoh et al. |
| 2004/0170685 A1* | 9/2004 | Carpenter et al. ............ 424/468 |
| 2005/0079196 A1 | 4/2005 | Henkes et al. |
| 2005/0222603 A1* | 10/2005 | Andreas et al. ............ 606/194 |
| 2006/0036281 A1 | 2/2006 | Patterson et al. |
| 2008/0045922 A1 | 2/2008 | Cragg et al. |
| 2008/0051803 A1 | 2/2008 | Monstadt et al. |
| 2008/0103585 A1 | 5/2008 | Monstadt et al. |
| 2008/0125855 A1 | 5/2008 | Henkes et al. |
| 2008/0228215 A1 | 9/2008 | Strauss et al. |
| 2008/0228216 A1 | 9/2008 | Strauss et al. |
| 2008/0319532 A1 | 12/2008 | Monstadt et al. |
| 2009/0254111 A1 | 10/2009 | Monstadt et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0076479 A1 | 3/2010 | Monstadt |

OTHER PUBLICATIONS

Middleton, J.C. & Tipton, A.J. Synthetic biodegradable polymers as orthopedic devices, Biomaterials 21, 2335-46 (2000).

Co-Pending U.S. Appl. No. 10/597,299, filed Jul. 19, 2006, Monstadt.

Co-Pending U.S. Appl. No. 12/543,857, filed Aug. 19, 2009, Sutherland et al.

International Preliminary Report on Patentability issued on Nov. 21, 2006 to a related international application No. PCT/US2005/018087 in 16 pages.

International Search Report issued Dec. 16, 2005 to a related international application no. PCT/US2005/18087 in 7 pages.

Communication under Rule 71(3) EPC (Notice of Allowance) in European Patent Application No. 05756033.6 dated Jul. 5, 2010 in 6 pages.

International Preliminary Report on Patentability issued on Nov. 21, 2006 to a related international application.

International Search Report issued Dec. 16, 2005 to a related international application.

* cited by examiner

METALLIC COILS ENLACED WITH BIOLOGICAL OR BIODEGRADABLE OR SYNTHETIC POLYMERS OR FIBERS FOR EMBOLIZATION OF A BODY CAVITY

This application claims priority to Provisional Application No. 60/573,710 filed May 21, 2004 which is incorporated by reference in its entirety.

FIELD OF THE INVENTION

This invention relates to vaso-occlusion devices for forming an occlusion (embolism) at a desired vascular location, in particular at the site of an aneurism. The devices are helical wire coils preferably with enlaced fibrous materials providing an increased surface area to facilitate high rates of desired bioactions such as bioactive material release or embolic interactions between the device's surface and the patient's bloodstream. The coils may be coated with at least a single layer including a bioactive material.

BACKGROUND

Body cavity embolism (e.g. brain blood vessel aneurysm occlusion by detachable coils, liquid embolism, particle embolism, balloon embolism) is a treatment that may have a high incidence of recurrence. Due to insufficient healing at the aneurysm/parent artery interface, mechanical and biological forces, incompletely understood, create a new expansion of aneurysm. That is the aneurysm reforms or recurs after endovascular, embolic treatment.

In one treatment Pt/Ir coils are packed in aneurysms so that they occupy ~20% to 30% of the aneurysm volume and reduce the inflow of blood into the aneurysm. Aneurismal blood, at 70% to 80% by volume, clots by stagnation. Preferably, the clotted blood organizes and proceeds through a series of steps similar to those occurring at any wound in the body: (1) hemostasis, (2) inflammation, (3) tissue formation, and (4) remodeling. An aneurysm so treated is excluded from the arterial circulation. On the other hand, for partially understood reasons, the clotted blood may not organize, the coil mass compacts and/or new blood flow—coupled with the diseased arterial tissue—allows expansion of the aneurysm. Thus the aneurysm recurs and remains susceptible to rupture and hemorrhagic stroke.

With the pursuit of tissue engineering, devices were created that attempt to direct or enhance the healing of the aneurysm/artery interface rather than rely on each patient's individual reaction to the embolism of the an aneurysm cavity. Embolic devices, such as electrolytically-detached Pt/Ir coils, have been designed with coatings that swell in aqueous solution or that provoke a mild inflammatory response.

One form of device contains a polyacrylamide hydrogel attached to the Pt/Ir detachable coil. As the coil resides in blood, the hydrogel swells and occupies more space than bare metal coils, leading to higher packing densities (~40% to 50%).

Other coils use the biodegradable polymer PGLA (poly glycolyic/lactic acid—the same material used in absorbable sutures) as a bioactive coil coating to provoke a mild inflammatory response in the aneurysm that triggers aneurismal organization per the above wound healing steps.

Both approaches suffer from the same problem: they are limited by the small size of these coils and the fact that the coils must be delivered through a microcatheter with the smallest ID of ~0.015". Coils may have a minimum of 0.09 cm of surface area (0.011" OD, over a 1 cm length). Placing a coating, hydrogel or bioactive coating, and ensuring that the treated coil can move through a 0.015" ID catheter places a finite limit on the amount of hydrogel or bioactive coating applied to the coil. In general, the amount of material is limited by the surface of the coil and the delivery catheter. Limited to no efficacy data exist for the coated coils. However, physician feedback indicates that the results are no better than bare-metal coils.

Helical coils are one form of device that has been extensively employed. Hans Henkes, et al., NEUROSURGERY 54, No. 2, 268 (2004) describe the results of over 1800 procedures involving helical coils and conclude that such devices are safe and efficacious for occlusion for patients with intracranial aneurysms.

A number of variations on helical coils have been proposed heretofore. For example, U.S. Pat. No. 5,226,911 issued to Chee and Narient describes looping 5 to 100 biocompatible polymer fibers through the helical coils. Dacron, polyglycolic acid, polylactic acid, fluoropolymers, nylon and silk are among the polymers suggested for these fibers. U.S. Pat. No. 5,382,259 issued to Phelps and Van describes braided or woven fibrous tubular coverings with and without tassels for helical coils. U.S. Pat. No. 5,549,624 issued to Mirigian and Van describes a helical coil device with added fibrous loops which are described as increasing the device's thrombogenicity. U.S. Pat. No. 5,658,308 issued to Snyder describes a helical metal device with from one to several hundred axial fibrous strands passing through its center and optionally filaments attached to the windings of the coil. These filaments are recited to be bioactive or nonbioactive and to enhance the ability of the coil to occlude the site at which it is placed. U.S. Pat. No. 5,935,145 issued to Villar and Aganon describes helical coils two fibrous members, each of a different material, attached. One of the materials is preferably biodegradable. The other is preferably not biodegradable. U.S. Pat. No. 6,299,627 issued to Eder et al. describes devices with coils or braids and two coatings including an inner coating and another coating selected to affect the solubility of the inner coating.

All of this work suggests that although helical coil inserts are attractive vasoocclusive devices there are opportunities to improve their performance to achieve optimal performance in terms of ease of delivery to and placement at the treatment site and in terms of the degree and rate of vaso-occlusion achieved.

SUMMARY OF THE INVENTION

Statement of the Invention

We have now discovered improvements to vaso-occlusion devices comprised of a coil, e.g., a metallic coil enlaced with biological, biodegradable or synthetic polymer fibers.

A need exists for an embolic device that can increase the effective surface area so that higher levels of biological, biodegradable, or synthetic agents can be present to embolize a body cavity and direct or provoke a healing response.

We sought to provide more surface area to an embolic coil device by adding fibers. By increasing initial blood contact surface area between aneurismal blood and tissue, bioactive agents (biological, biodegradable, or synthetic) can be used at higher concentrations or in greater amounts than previously used. The same concentration or amount can be spread over a larger contact surface area.

More particularly, we have discovered that providing a large but controlled additional surface area to a helical coil device in the form of fibers enlaced into the coil provides an improved device. The amount of additional surface area provided by the enlaced fibers should be at least 0.1 times the surface area provided by the metallic coil itself, to as much as 10 or greater times the surface area provided by the metallic coil itself.

Thus, this invention provides a vaso-occlusion device comprising:

(a) a helical coil of 0.025 mm or larger metal wire, the coil sized for insertion to a point of use in the vascular network of a patient for occluding blood flow and having a plurality of windings and having a first surface area and (b) a plurality of fibrous elements enlaced through the helical coil and having outwardly extending ends, said fibrous elements presenting a bioactive outer surface and collectively having a second surface area with the second surface area being at least 0.1 times the first surface area.

In one embodiment the majority of the fibrous elements each enlace a single winding of the helical coil. In additional embodiments the majority of the fibrous elements each enlace two or more windings of the helical coil.

The fibrous elements can be made of a bioactive material or a nonbioactive material. They can be stable in the conditions of use or they can undergo biodegradation in that setting. They can include a coating of bioactive material on a core of nonbioactive material or on a core of bioactive material. They may include a coating comprised at least partially of a non-bioactive material. The bioactive material can be a naturally-occurring material or a synthetic material. Synthetic material may include any material made by the human hand including, but not limited to engineered versions of naturally occurring material, e.g., molecules.

An exemplary family of materials for forming the fibers or for coating the fibers include copolymers of glycolic acid with lactic acid copolymers.

In other embodiments this invention provides methods of producing these devices by enlacing fibers, before or after coating, into the helical coils as well as methods for treating a patient to embolize a body site by placing a device of this invention at the site in need of embolization.

BRIEF DESCRIPTION OF THE DRAWINGS

This invention will be further described with reference being made to the accompanying drawings in which:

FIG. 7b is a not-to-scale top view of the embodiment of the invention shown in FIG. 7a.

DETAILED DESCRIPTION OF THE INVENTION

Figure 1:
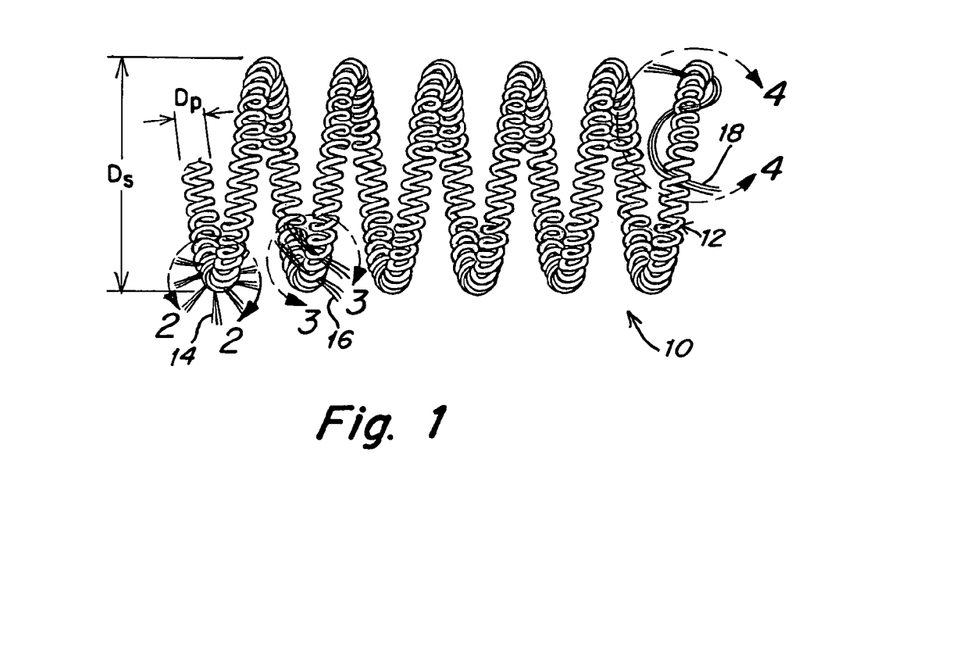
FIG. 1 is a not-to-scale side view of a vaso-occlusive coil showing three representative embodiments of the fibers which are present enlaced into it. Three areas are identified in FIG. 1. Area 2-2' shows an embodiment where the fibers are enlaced around a single loop of the coil. Area 3-3' shows an embodiment where the fibers are enlaced through a single loop of the coil. Area 4-4' shows an embodiment where the fibers are enlaced through a plurality of loops of the coil.

This detailed description is broken down into the following sections.
Metal Coils and Device Configurations
Stretch Resistant Members
Fiber Materials
Bioactive Materials
Applications Metal Coils and Device Configurations The vaso-occlusion devices of this invention are made up of a coil, e.g. a metal coil preferably with enlaced fibers pendant therefrom. In certain embodiments the devices are in the form of a helix and may be comprised of a simple single helix. In other embodiments, however, the coils are coils on coils having a primary helical coil wound into a secondary helix or other secondary shape with fibers enlaced through the primary coil such as shown in FIG. 1. In FIG. 1 a device 10 is shown having a metal coil 12 having a large or secondary helix having a diameter Ds and a small or primary helix having a diameter Dp. A plurality of fibers 14, 16, and 18 are shown enlaced through the coils of the primary helix in configurations captured in lines 2-2', 3-3' and 4-4' and thereafter depicted in expanded scale in FIGS. 2, 3, 3A and 4 respectively. It will be appreciated that these four enlacing configurations are merely representative and that equivalent configurations which suitably associate the fibers with the coils are also contemplated within the scope of this invention.

The wire making up the coil 12 may be a biocompatible metal, that is a metal that does not react adversely with the tissues and fluids it comes in contact with when used in the body. The metals may also be radio opaque so that the position and location of the coils in the body can be monitored with radiological techniques. Suitable metals include, but are not limited to the noble metals such as the platinum group metals which include platinum, palladium, rhodium and rhenium as well as iridium, gold, silver, tungsten, and tantalum and alloys of these metals with one another. Additional useful metals may include the super elastic metals such as "Nitinol" and the like. These materials are described in the art such as in U.S. Pat. Nos. 3,174,851 and 3,753,700 and can include nickel-titanium alloys having about 0.4 to about 0.5 molar fraction nickel and 0.5 to 0.6 molar fraction titanium; aluminum-nickel alloys having about 0.35 to 0.4 molar fraction aluminum; and the like. Platinum-iridium and platinum-tungsten alloys having predominant fractions of platinum are most preferred metals.

The metal component may be comprised of a wire. In certain embodiments the wire commonly has a diameter of from about 0.025 to about 0.09 mm, from about 0.03 to about 0.08 mm from about 0.04 to about 0.06 mm. In certain specific embodiments the wire has a diameter of about 0.05 mm.

In some embodiments the wire may be comprised only of a primary shape e.g., a simple single helix. In some embodiments the wire component may comprise a primary shape e.g., helical coil and a secondary shape. The secondary shape may comprise a complicated three dimensional shape. In other embodiments the wire can comprise a coil of coils or double helix. When it is a coil of coils, the outer or secondary diameter of the outer helix may be from about 1 to about 25 mm in some embodiments and from about 2 to 20 mm in certain other embodiments. The primary (inner) helix may typically have an outside diameter of from about 0.1 to about 0.8 mm in some embodiments, and from about 0.15 to about 0.6 mm in other embodiments and from about 0.2 to about 0.4 mm in yet other embodiments. Certain specific embodiments provide for coils having a primary diameter of about 0.28 mm sized to pass through a correspondingly dimensioned catheter. Yet other embodiments provide for coils having a primary diameter of about 0.24 mm sized to pass through a correspondingly dimensioned catheter.

Figure 2:
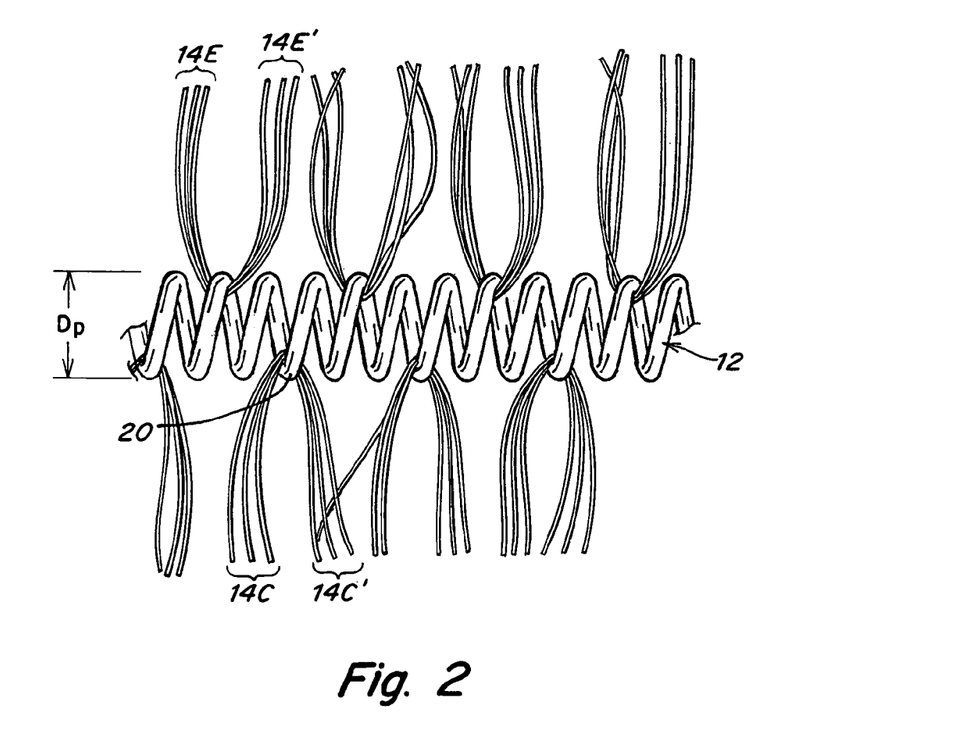
FIG. 2 is an expanded scale view of the 2-2' area of FIG. 1 which shows an embodiment where the fibers are enlaced around a single loop of the coil.
Figure 3:
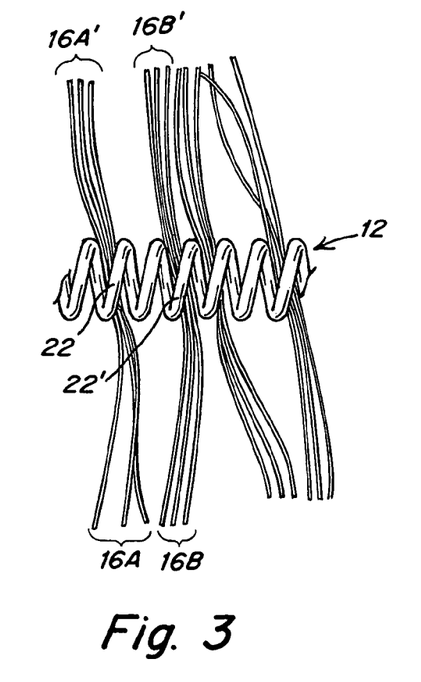
FIG. 3 is an expanded scale view of the 3-3' area of FIG. 1 which shows an embodiment where the fibers are enlaced through a single loop of the coil.

The secondary helix may have from about 0.5 to about 20 windings per cm in some embodiments and from about 1 to about 10 windings per cm in other embodiments. The inner or primary coil may have from about 2 to about 50 windings per mm in some embodiments and from about 5 to about 40 windings per mm in other embodiments. These primary coil winding values are determined on the primary coil without added fibers. As fibers are added they typically expand the primary helix to some degree as they enlace through the primary helical coils. Thus, in FIGS. 1, 2, 3 and 4 the primary helix coils are depicted with a pitch that allows for free space between adjacent coils. As shown in FIGS. 2 and 3, for example, this extra spacing between the coils is shown to make up to about 60% of the overall secondary helix length. While this configuration is certainly acceptable in many settings, in other settings it may be desirable to have the spacing between the coils small enough (or nonexistent) so as to permit the fibers, when added, to distort the coil and permit the coil to apply pressure to grip the fibers and hold them in place. This latter situation is referred to as a "fiber gripping" configuration for the primary coil. Accordingly, in certain embodiments the extra spacing between adjacent primary coil windings can range from about 0% to about 80% of the overall unstretched primary helix length. A fiber-gripping configuration may be achieved when the extra spacing between adjacent coils is in the range of from about 0% to about 25% of the total length.

The unstretched overall axial length of the devices of this invention ranges from about 5 to about 400 mm in some embodiments and from about 10 to about 300 mm in other embodiments. This length may be selected depending upon the particular application of use and may be longer than 400 mm in some embodiments.

As can be seen in FIGS. 1 through 7, there are many possible configurations for the fibers which are present in the devices of the invention. The materials making up these fibers will be described in the section entitled Fiber Materials. The configuration of the fibers is set forth below.

In certain embodiments, the fibers that comprise part of the devices of the invention are enlaced through the primary coils of the helixes. In other embodiments the fibers that comprise part of the devices of the invention are wrapped at least twice around a stretch resistant member disposed within the central lumen of the coil, typically attached at each end thereof. In some embodiments the fiber may be tied to the coil or the stretch resistant member, e.g., via a knot. The fiber may be tied and laced around the coil or the stretch resistant member or both. In other embodiments the fiber is not tied or knotted, but is laced or wound around the coil or the stretch resistant member or both. The fibers may be flexible and may be cut to shorter lengths to accommodate coil delivery through a microcatheter.

As shown in FIG. 2, one suitable lacing configuration may include fibers laced around a single coil 20 of the primary helix with both ends of a single fiber 14 extending radially from the coil 12 in the same general direction. This can occur with a single fiber such as 14c-14c' or with a plurality of fibers 14e-14e'. The fibers may be comprised of monofilaments or yarns. The fibers may be comprised of single fibers or bundles of associated fibers. The bundles of fibers may range from two fibers to about 50 fibers or more. The fibers are not drawn to scale in any of these drawings. In certain embodiments, they may extend from the secondary coil at least about 0.05 mm. In other embodiments they may extend from the secondary coil about 0.05 to about 5 mm. In yet other embodiments they may extend from the secondary coil about 0.5 mm to about 4 mm. As will be apparent, these dimensions are relatively small as compared to Ds shown in FIG. 1, but comparable to or larger than Dp. The fibers may have diameters ranging from about 0.01 mm to about 0.60 mm in some embodiments. In other embodiments the fibers may have diameters ranging from about 0.02 mm to about 0.05 mm. In the case of yarn, the overall yarn diameter will typically be in these ranges with the individual filaments making up the yarn being smaller in diameter.

As noted previously, it is often advantageous for the diameter of the fiber or bundle of fibers to exceed the space between windings of the primary helix so that the space is a fiber-gripping distance.

As shown in FIG. 3, one embodiment of the invention contemplates enlacing the fibers 16 such that they extend out of opposite sides of the primary winding 12. In this embodiment a single fiber 16a-16a' can enlace and pass by a single coil 22 of helix 12. Similarly a bundle of fibers 16b-16b' can enlace and pass by a single coil 22'. In this configuration it is advantageous to have the spacing between adjacent windings of the primary coils to be a fiber-gripping distance. The fibers in this embodiment may be of similar dimensions to those set forth in FIG. 2.

Figure 3A:
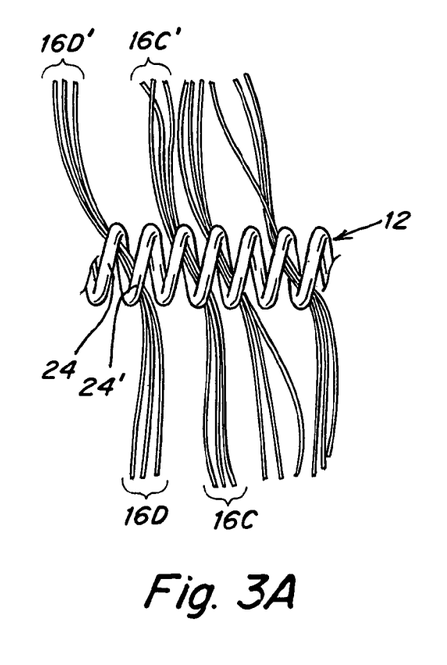
FIG. 3A is an expanded scale view of the 3-3' area of FIG. 1 which shows an embodiment where the fibers are enlaced through a pair of loops of the coil.

As shown in FIG. 3A, variations on the lacing pattern of FIG. 3 are contemplated. Thus, a bundle of fibers 16-16c' or an individual fiber 16d-16d' may be laced through a pair of adjacent coils 24 and 24' in the primary helix. This configuration may advantageously provide a fiber-gripping spacing between adjacent coils.

Figure 4:
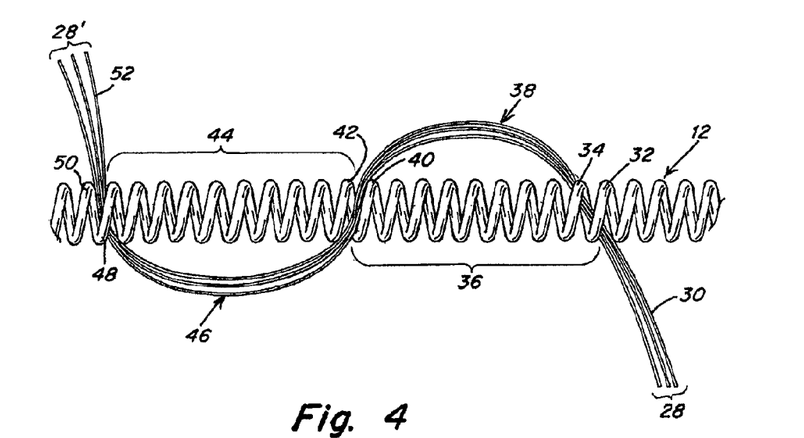
FIG. 4 is an expanded scale view of the 4-4' area of FIG. 1 which shows an embodiment where the fibers are enlaced in an "S" pattern through a plurality of loops of the coil.
Figure 5:
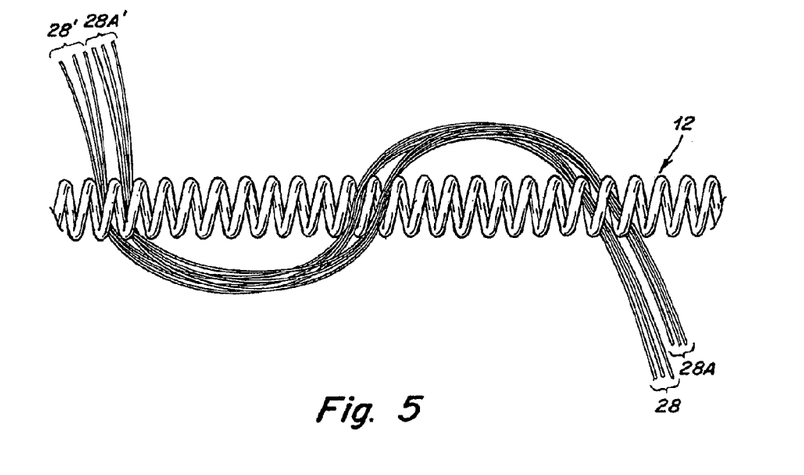
FIG. 5 is an expanded scale view similar to FIG. 4 with a variation in the way the fibers are enlaced. In this embodiment two sets of fibers are enlaced adjacent to each other in "S" patterns on the coil.

As shown in FIGS. 4 and 5, the fibers that are enlaced through the primary helix of the coil may be enlaced back and forth across the coil in an "S" configuration to facilitate gripping of the fibers by the coil and minimize the likelihood that they are dislodged in use. In FIG. 4, a bundle of fibers 28 first laces though windings 32 and 34 of coil 12 leaving a tail 30 extending a suitable distance as set forth above. Next the bundle 28 forms loop 38 spanning a number of windings 36. This number may be as small as one winding or may be as large as 10-12 windings. In certain embodiments the number of windings may be substantially larger than 12. Thus certain embodiments of the invention provide at least one winding looped by a fiber, e.g. 38 in FIG. 4. Then the fibers may be enlaced through windings 40 and 42 and out the other side of coil 12 to form a corresponding opposite loop 46 which spans a number of windings 44 which may be about the same as the number of windings described for 38. The fibers may then be enlaced through windings 48 and 50 and end at 28' to form a tail 52 similar to tail 28.

FIG. 5 shows that multiple bundles forming the double looped "S" configuration 28 and 28A through 28' and 28A' are also contemplated. These multiple loops may be arrayed parallel to one another and enlace adjacent windings as depicted in FIG. 5 but may also vary from one another and be more random, if desired.

Stretch Resistant Members

Figure 7A:
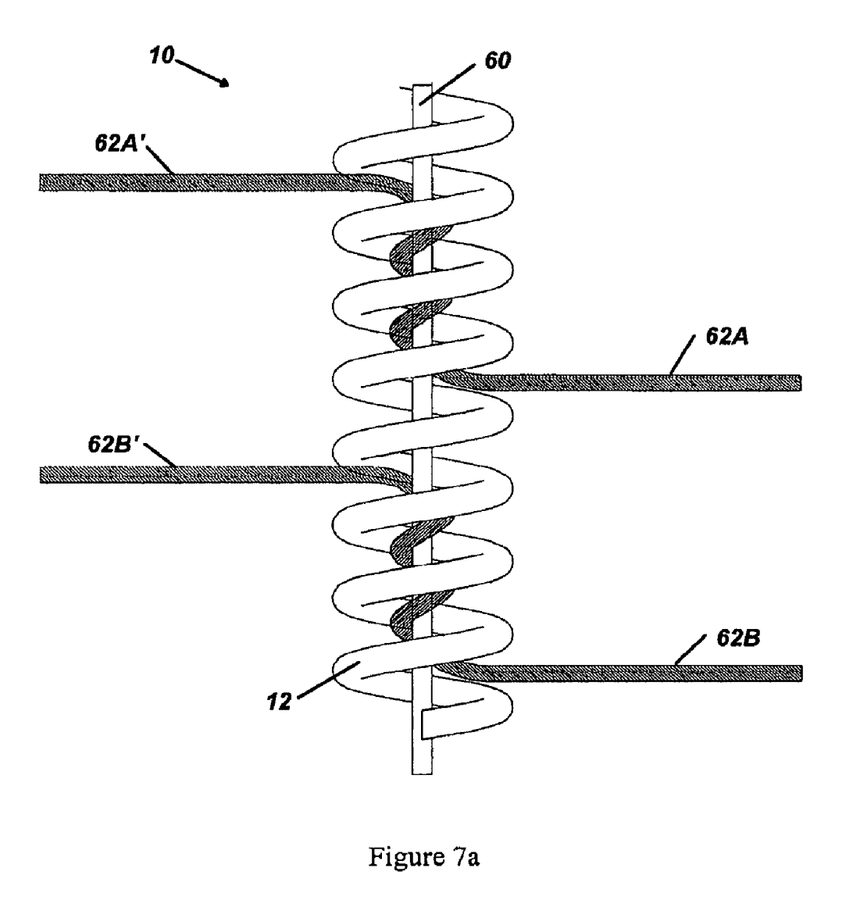
FIG. 7a is a not-to-scale side view of an example of one embodiment of the invention comprising a vaso-occlusive coil which includes a stretch resistant member fixedly attached to the coil and a plurality of fibers, where each fiber is wrapped around the stretch resistant member at least twice.
Figure 7B:
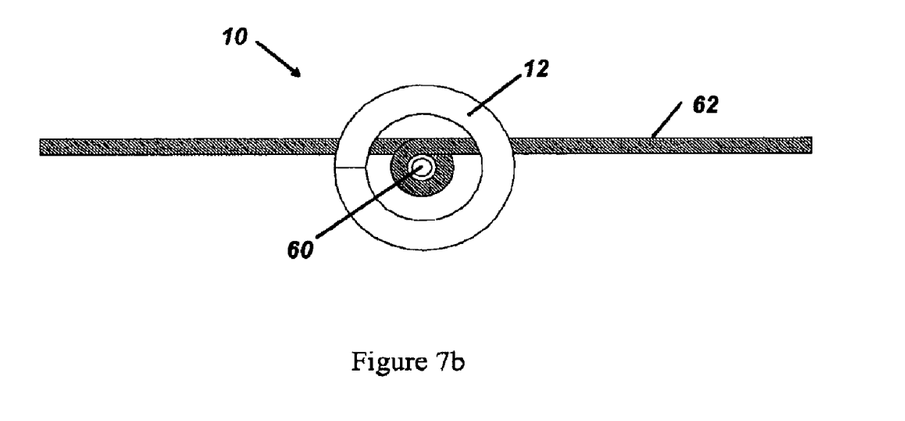

The device 10 of one embodiment of the invention may be comprised of a stretch resistant member 60. The stretch resistant member 60 may prevent movement or elongation or deformation of the device 10 e.g., during retrieval or repositioning. The stretch resistant member 60 may be fixedly attached to at least one end of the device 10. In certain embodiments it may be fixedly attached to both ends of the device 10. In some embodiments, the stretch resistant member 60 may axially traverse the interior region or lumen of the coil 12.

The stretch resistant member 60 may be made from a wide variety of materials. These include any of the materials, e.g., metals, described as suitable for making the coil 12. The stretch resistant member 60 may be comprised of a radiopaque material. It may also be comprised of a polymer.

In certain embodiments at least one fiber 62 is wrapped at least two times round the stretch resistant member 60. In certain embodiments the invention provides for a plurality of fibers 62A, 62A', e.g. at least one bundle 62B, 62B' or a plurality of bundles 62B, 62B' wrapped at least two times round the stretch resistant member 60. Wrapping the fiber around the stretch resistant member 60 at least twice advantageously provides a means of securing at least one fiber 62 to the device 10. In certain embodiments the fiber 62 may not be tied or knotted to the device 10 thereby avoiding potentially obstructive bundles which might hinder deployment of the device 10 or might mechanically damage the device 10.

Fiber Materials

In certain embodiments, the fibers may be comprised of polymeric materials. The polymeric materials may include materials approved for use as implants in the body or which could be so approved. They may be nonbiodegradable polymers such as polyethylene, polyacrylics, polypropylene, polyvinylchloride, polyamides such as nylon, e.g., Nylon 6.6, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. In certain specific embodiments the nonbiodegradable materials for the polymer component may comprise polyesters, polyethers, polyamides and polyfluorocarbons.

The polymers can be biodegradable as well. Representative biodegradable polymers include:
polyglycolic acid/polylactic acid (PGLA),
polycaprolactone (PCL),
polyhydroxybutyrate valerate (PHBV),
polyorthoester (POE),
polyethyleneoxide/polybutylene terephthalate (PEO/PBTP),
polylactic acid (PLA),
polyglycolic acid (PGA),
poly(p-dioxanone),
poly(valetolactone),
poly(tartronic acid),
poly(β malonic acid),
poly(propylene fumarate),
poly(anhydrides); and
tyrosine-based polycarbonates.

Other equivalent materials, including but not limited to stereoisomers of any of the aforementioned, may be used as well.

In certain embodiments the biodegradable polymer may be comprised of copolymers of lactic acid and glycolic acid. The copolymer may be comprised of glycolic/lactic acid in the ratio of 90:10. In certain embodiments the ratio of glycolic to lactic acid is chosen from 99:1; 90:10; 95:5; 50:50; 10:90; 5:95; 1:99. In one embodiment the fibers may be comprised of Nylon 6.6

Using polyglycolide and poly(L-lactide) as base materials it is possible to copolymerize the two monomers to extend the range of homopolymer properties. Copolymers of glycolide with both L-lactide and DL-lactide have been developed for both device and drug delivery applications. It is noteworthy that there is not a linear relationship between the copolymer composition and the mechanical properties of the materials. For example a copolymer of 50% glycolide and 50% DL-lactide degrades faster than either homopolymer. (See, Middleton and Tipton, 2000, *Biomaterials* 21:2335, which is incorporated herein by reference).

The fibers may be coated with at least a single coating of bioactive material (e.g. growth factors, genes, collagen, peptides, oligonucleotides, marine biopolymers such as chitosan, various mono-, di-, and poly-saccharides such as hyaluronic acid and the like or combinations thereof). In some embodiments a plurality of coatings is contemplated. The fibers may be coated with a non-bioactive material, or a combination of bioactive and non-bioactive material applied as a single layer or a plurality of layers.

Bioactive Materials

Figure 6:
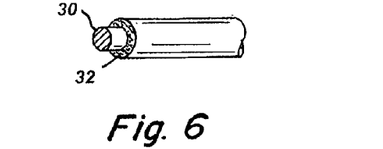
FIG. 6 is a not-to-scale partial cross section of a type of fiber or a type of coil useful in the present invention having a core and an outer coating.

In some embodiments, the fibers can include within their body a bioactive material. In other embodiments, the bioactive material can be present in a coating applied to the coil, the stretch resistant member, or to the fibers or to any combination of the three. In one embodiment of this invention, the bioactive coating may be applied to the coil as a single layer and the fibers with or without bioactive coating can be omitted. In other embodiments, however, the bioactive material is dispersed in the fiber or coated on the fiber. As shown in FIG. 6 this configuration involves a core of metal coil or fiber 30 with single outer coating comprising bioactive material 32.

The bioactive material, e.g., coatings may be proteinaceous e.g., a collageneous coating. Collageneous coatings may be of a wide variety of types, including natural or synthetic. In specific embodiments the bioactive material comprises a photo polymerizable collagen coating which will bind both with the metal with or without added bioactive agents. Examples of suitable collageneous materials include those having the same surface functional groups as do Type I and Type IV natural collagens.

The bioactive material or agent present in the polymer itself or the coating if present may have one or more functions, including, but not limited to, reducing friction, providing a therapeutic for local or blood borne delivery, or reducing thrombosis, coagulation or platelet activity. The bioactive material may be hydrophilic, e.g. a lubricious hydrophilic material such as hyaluronic acid. Examples of suitable hydrophilic compounds include polyvinyl alcohol (PVA), polyvinylpyrrolidone (PVP), polyacrylamide and the like. The bioactive material may be hydrophobic. Hydrophobic compounds include membrane lipids such as phosphatidyl choline, fatty acid esters and the like. The bioactive material may include water soluble therapeutics. Examples of water-soluble therapeutics include thrombolytics such as tissue plasminogen activator (TPA), streptokinase, urokinase, hirudin and growth factors such as vEGF. The bioactive material may include fat soluble therapeutics, e.g., fat soluble vitamins.

The bioactive coating or material may also promote cell attachment. It may also be thrombogenic. Non-limiting examples of bioactive coatings or materials which increase cell attachment and/or thrombogenicity include both natural and synthetic compounds, e.g. collagen, fibrinogen, vitronectin, other plasma proteins, growth factors (e.g. vascular endothelial growth factor, "vEGF"), synthetic peptides of these and other proteins or peptides having attached RGD (arginine glycine-aspartic acid) residues, generally at one of both termini or other cell adhesion peptides, i.e., GRGDY, oligonucleotides, full or partial DNA constructs, natural or synthetic phospholipids or polymers with phosphorylcholine functionality.

Applications

The devices of this invention may be introduced to a selected site and thus the device of the invention may be used in treating a variety of maladies. For instance, in treatment of an aneurysm, the aneurysm itself may be filled with a plurality of devices. Alternatively, only one device may be administered. Shortly after the devices are placed within the aneurysm, an emboli may begin to form optionally under the influence of the bioactive material.

A selected site may be reached through the vascular system using a collection of specifically chosen catheters and guide wires. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter are then placed though the guiding catheter as a unit. Once the tip of the guidewire reaches the end of the guiding catheter, it is then extended by the physician, with the aid of fluoroscopy to the site to be treated using the vaso-occlusive devices of this invention. The guidewire is advanced first from the guide catheter tip to the treatment site, followed by the neurovascular catheter. Once both the distal tip of the neurovascular catheter and the guidewire have reached the treatment site, and the distal tip of that catheter is approximately situated, e.g. within the mouth of an aneurysm to be treated, the guidewire is then withdrawn. The neurovascular catheter then has an open lumen to the outside of the body. The device of the invention is then pushed through the lumen to the treatment site and detached from the catheter. The device may be held in place because of its shape, size or volume.

EXAMPLES

Example 1

Adding Fibers

A T-10 platinum coil is obtained and fastened to a flat surface at its ends. It has a primary helix diameter of 0.028 mm. A plurality of Vicryl 90/100 PGLA sutures with diameters of from 0.099 mm to 0.029 mm are obtained. These sutures are made up of a bundle of 6-7 small microfibers about 12 μm in diameter. A single monofilament of similar size could also be employed. The fibers are cut into about 2 cm lengths and physically enlaced in between windings of the T-10 coil in the configurations shown in FIGS. 2-5. This is done until a total of about 10-20 fibers per cm extend away from the coils. The fibers are trimmed to have 2-4 cm lengths extending from the coils.

If the fibers are coated with bioactive material or if they contain bioactive material, the surface area provided by the fibers would enhance delivery and activity.

Example 2

Coating

1. Fill an ice container with cold water and add ice as needed to reach a temperature of 4-6° C.
2. Submerge a 15 ml centrifuge tube rack into the container/bucket.
3. Place 15 ml centrifuge tubes (filled with collagen solution at pH 7.4±2) into the centrifuge rack
4. Pass a platinum coil through a drilled centrifuge cap into the solution.
5. Allow the coil to remain in the solution for 20 minutes.
6. Remove the coil and tube (ensure that the coil remains in the collagen solution) from the ice container/bucket.
7. Place the coil(s) in a 37° C. oven for 4 hours.
8. Remove the coil from the collagen solution and rinse the coil 3× in PBS and 3× in distilled water.
9. Allow the coated coil to dry overnight.

What is claimed is:

1. A vaso-occlusive device for occluding blood flow in a patient, the device comprising:
    a coil, comprising a lumen and a first and a second end, and sized for insertion to a point of use in a vascular network of the patient;
    a stretch resistant member having a first end fixedly attached to the first end of the coil and a second end fixedly attached to the second end of the coil; and
    a plurality of fibers where each of the fibers is in direct contact with the stretch resistant member, wherein each of the fibers is wrapped around the stretch resistant member at least two times, wherein each of the fibers comprises a first fiber end and a second fiber end, the first fiber end moving independently and extending freely of the coil, the second fiber end moving independently and extending freely of the coil.

2. The device of 1, wherein the stretch resistant member axially traverses the lumen of the coil.

3. The device of claim 1, wherein the stretch resistant member comprises a metal wire.

4. The device of claim 3, wherein the metal wire comprises a metal chosen from the group consisting of platinum, palladium, rhodium, rhenium, iridium, gold, silver, tungsten and tantalum, an alloy of two or more of these metals and a superelastic metal.

5. The device of claim 1, wherein the stretch resistant member comprises a polymer.

6. The device of claim 5, wherein the polymer is one of non-biodegradable and biodegradable.

7. The device of claim 1, wherein the stretch resistant member further comprises a bioactive coating.

8. The device of claim 7, wherein the bioactive coating is chosen from the group consisting of a growth factor, a gene, an oligonucleotide, a peptide, a marine biopolymer, a mono-saccharide, a di-saccharide, a poly-saccharide, collagen and combinations of any of the aforementioned.

9. The device of claim 7, wherein the bioactive coating comprises a polymer.

10. The device of claim 1, wherein the coil comprises metal wire.

11. The device of claim 10, wherein the metal wire comprises a metal chosen from the group consisting of platinum, palladium, rhodium, rhenium, iridium, gold, silver, tungsten, tantalum, an alloy of two or more of these metals and a superelastic metal.

12. The device of claim 1, wherein the coil comprises a primary helix which is itself wound into a secondary shape.

13. The device of claim 12, wherein the secondary shape is a helix.

14. The device of claim 1, wherein the fibers comprise one of a bioactive and a non-bioactive material.

15. The device of claim 1, wherein the fibers comprise a copolymer of glycolic acid and lactic acid.

16. The device of claim 1, wherein the fibers further comprise a bioactive coating.

17. The device of claim 16, wherein the bioactive coating is one of a lubricious hydrophilic coating and a hydrophobic coating.

18. The device of claim 16, wherein the bioactive coating comprises a copolymer.

19. The device of claim 18, wherein the copolymer comprises lactic acid and glycolic acid.

20. The device of claim 1, wherein the fibers comprise a non-biodegradable polymer.

21. The device of claim 20, wherein the non-biodegradable polymer is chosen from the group consisting of a polyethylene, a polyacrylic, a polypropylene, a polyvinylchloride, a polyamide, a polyurethane, a polyvinylpyrrolidone, a polyvinyl alcohol, a polyvinylacetate, a cellulose acetate, a polystyrene, a polytetrafluoroethylene, a polyester, silk, nylon, polyethylene terephthalate, and cotton.

22. The device of claim 1, wherein the fibers comprise a biodegradable polymer.

23. The device of claim 22, wherein the biodegradable polymer is chosen from the group consisting of polyglycolic acid, polycaprolactone, polyhydroxybutyrate valerate, polyorthoester, polylactic acid, poly(p-dioxanone), poly(valetolactone), poly(tartronic acid), poly(.beta.-malonic acid), poly(propylene fumarate), a tyrosine based polycarbonate, and a copolymer of polyethylene oxide and polybutylene terephthalate.

24. The device of claim 19, wherein a ratio of glycolic acid to lactic acid is one of the group consisting of 99:1, 1:99, 95:5, 5:95, 50:50, 90:10, and 10:90.

25. The device of claim 16, wherein the coating material is chosen from the group consisting of a growth factor, a gene, an oligonucleotide, a peptide, a marine biopolymer, a monosaccharide, a di-saccharide, a poly-saccharide, collagen and combinations of any of the aforementioned.

26. The device of claim 16, wherein the bioactive coating is applied to the coil and the stretch resistant member.

27. The device of claim 16, wherein the bioactive coating is applied to the fiber as a single layer.

28. The device of claim 26, wherein the bioactive coating is applied to the coil and the stretch resistant member as a single layer.

29. The device of claim 16, wherein the bioactive coating is dispersed throughout the fiber.

30. The device of claim 16, wherein the bioactive coating promotes cell attachment and is thrombogenic.

31. The device of claim 16, wherein the bioactive coating material is chosen from the group consisting of collagen, fibrinogen, vitronectin, vascular endothelial growth factor, and a peptide comprising the sequence arginine-glycine-aspartic acid (RGD).

32. The device of claim 1, wherein each of the first and second fiber ends extend radially outward from the coil.

33. The device of claim 1, wherein each of the fibers is wrapped around the stretch resistant member at least two times for securing the fibers to the device.

34. The device of claim 1, wherein each of the fibers is wrapped around the stretch resistant member at least two times for avoiding potentially obstructive bundles which might hinder deployment of the device or might mechanically damage the device.

35. The device of claim 10, wherein the metal wire comprises platinum.

36. The device of claim 20, wherein the non-biodegradable polymer comprises polypropylene.

37. The device of claim 20, wherein the stretch resistant member comprises polypropylene.

38. A vaso-occlusive device for occluding blood flow in a patient, the device comprising:
a coil, comprising a plurality of coil windings, a lumen and a first and a second end, and sized for insertion to a point of use in a vascular network of the patient;
a stretch resistant member having a first end fixedly attached to the first end of the coil and a second end fixedly attached to the second end of the coil; and
a plurality of fibers where each of the fibers is wrapped in direct contact around the stretch resistant member at least two times, the plurality of fibers being provided at discrete, spaced-apart intervals in between the coil windings along a length of the stretch resistant member.

39. The device of 38, wherein the stretch resistant member axially traverses the lumen of the coil.

40. The device of claim 38, wherein the stretch resistant member comprises a polymer.

41. The device of claim 38, wherein the coil comprises a primary helix which is wound into a secondary shape.

42. The device of claim 41, wherein the secondary shape is a helix.

43. The device of claim 38, wherein the fibers further comprise a bioactive coating.

44. The device of claim 43, wherein the bioactive coating promotes cell attachment and is thrombogenic.

45. The device of claim 38, wherein each of the fibers comprises first and second ends and each of the first and second fiber ends extends freely from the coil.

46. The device of claim 38, wherein each of the fibers is wrapped in direct contact around the stretch resistant member at least two times for securing the fibers to the device.

47. The device of claim 38, wherein each of the fibers is wrapped in direct contact around the stretch resistant member at least two times for avoiding potentially obstructive bundles which might hinder deployment of the device or might mechanically damage the device.

48. The device of claim 38, wherein the coil comprises platinum.

* * * * *

UNITED STATES PATENT AND TRADEMARK OFFICE
CERTIFICATE OF CORRECTION

| | | |
|---|---|---|
| PATENT NO. | : 7,896,899 B2 | Page 1 of 1 |
| APPLICATION NO. | : 11/134998 | |
| DATED | : March 1, 2011 | |
| INVENTOR(S) | : William R. Patterson et al. | |

It is certified that error appears in the above-identified patent and that said Letters Patent is hereby corrected as shown below:

Title page (Item 75) Inventors, Line 1: Change "Irvin, CA" for William R. Patterson to --Irvine, CA--.

In Column 1, Line 59: Change "glycolyic" to --glycolic--.

In Column 7, Line 59: Change "(valetolactone)," to --(valerolactone),--.

In Column 8, Line 7: Change "6.6" to --6.6.--.

In Column 10, Line 19 : Change "rack" to --rack.--.

In Column 10, Line 46, in Claim 2: Change "1," to --claim 1,--.

In Column 11, Line 39-40, in Claim 23: Change "(valetolactone)," to --(valerolactone),--.

In Column 12, Line 35, in Claim 39: change "38," to --claim 38,--.

Signed and Sealed this
Eighth Day of November, 2011

David J. Kappos
*Director of the United States Patent and Trademark Office*